(12) United States Patent
Sprichise et al.

(10) Patent No.: US 7,947,012 B2
(45) Date of Patent: May 24, 2011

(54) ASPIRATION CATHETER HAVING SELECTIVELY DEFORMABLE TIP

(75) Inventors: Matthew Spurchise, Peabody, MA (US); Thomas Nowak, Jr., North Hampton, NH (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 180 days.

(21) Appl. No.: 12/108,577

(22) Filed: Apr. 24, 2008

(65) Prior Publication Data

US 2009/0270800 A1 Oct. 29, 2009

(51) Int. Cl.
*A61M 31/00* (2006.01)
(52) U.S. Cl. .................................. 604/95.04
(58) Field of Classification Search ............... 604/95.04
See application file for complete search history.

(56) References Cited

U.S. PATENT DOCUMENTS

| | | | |
|---|---|---|---|
| 5,827,229 A | 10/1998 | Auth et al. | |
| 6,210,407 B1 * | 4/2001 | Webster | 606/41 |
| 7,507,229 B2 * | 3/2009 | Hewitt et al. | 604/527 |
| 2003/0093029 A1 | 5/2003 | McGuckin, Jr. et al. | |
| 2007/0060944 A1 | 3/2007 | Boldenow et al. | |
| 2007/0106211 A1 * | 5/2007 | Provost-Tine et al. | 604/96.01 |
| 2007/0276324 A1 | 11/2007 | Laduca et al. | |

* cited by examiner

*Primary Examiner* — Nicholas D Lucchesi
*Assistant Examiner* — Pritesh Patel

(57) ABSTRACT

An aspiration catheter includes an elastically deformable distal tip transformable between an orthogonal configuration and an oblique configuration to selectively and controllably appose the tip with thrombus or other matter to be aspirated. A core wire is slidably disposed in a core wire lumen within the catheter and is operably connected to the catheter distal tip. The core wire is controlled from the catheter proximal end to transform the distal tip between orthogonal and oblique configurations.

17 Claims, 8 Drawing Sheets

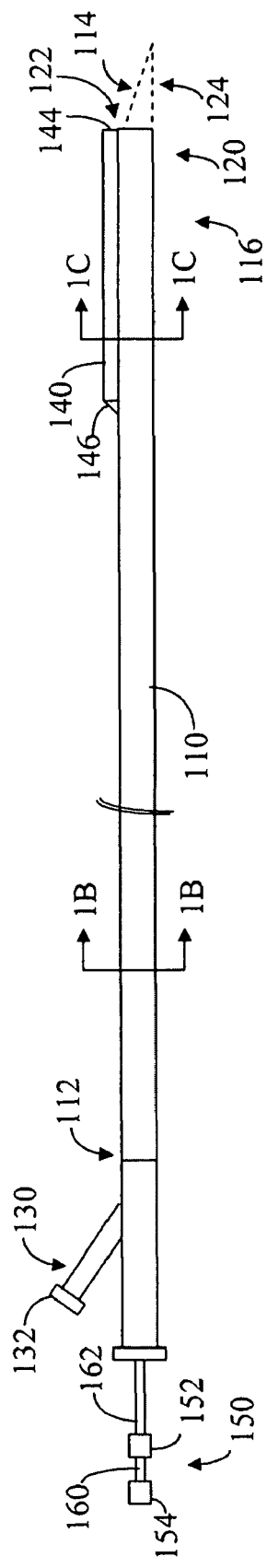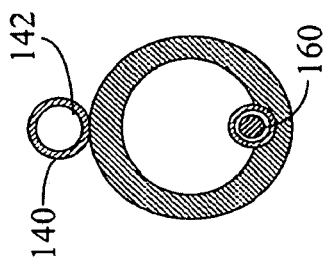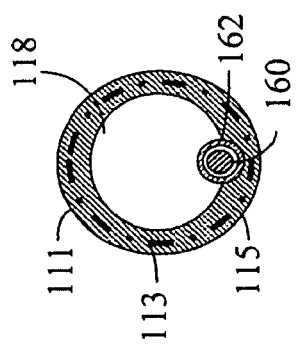

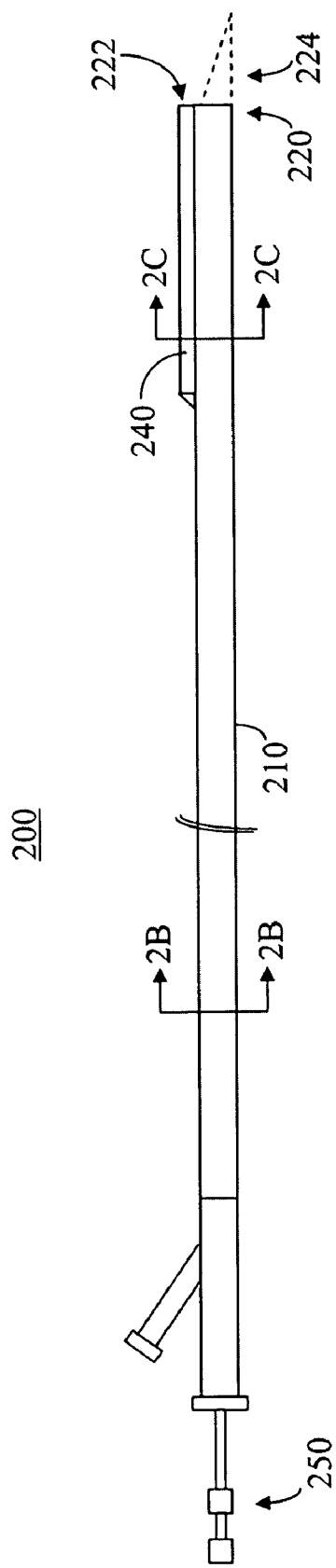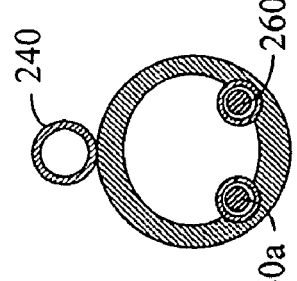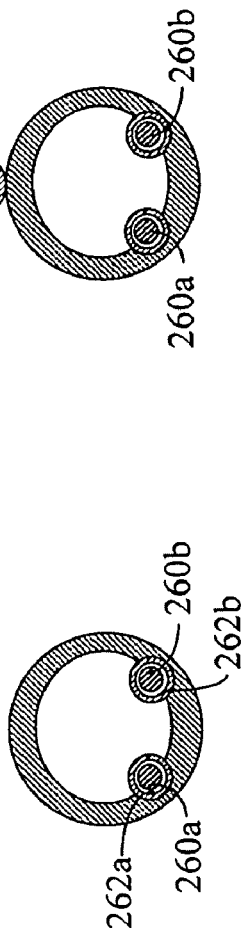

300

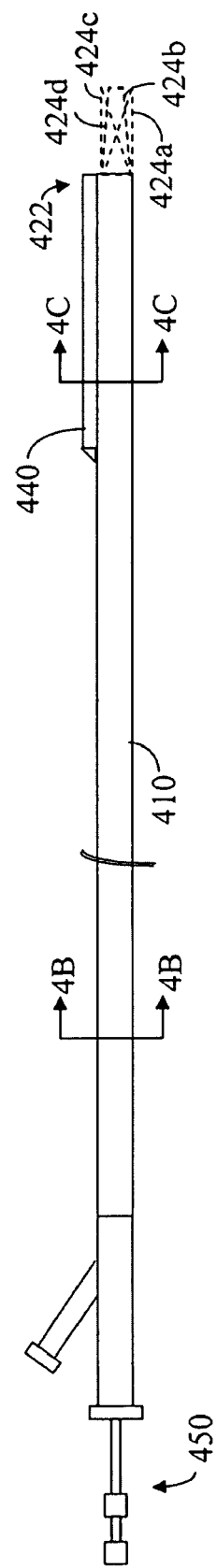
FIG. 4A
400
FIG. 4B
FIG. 4C

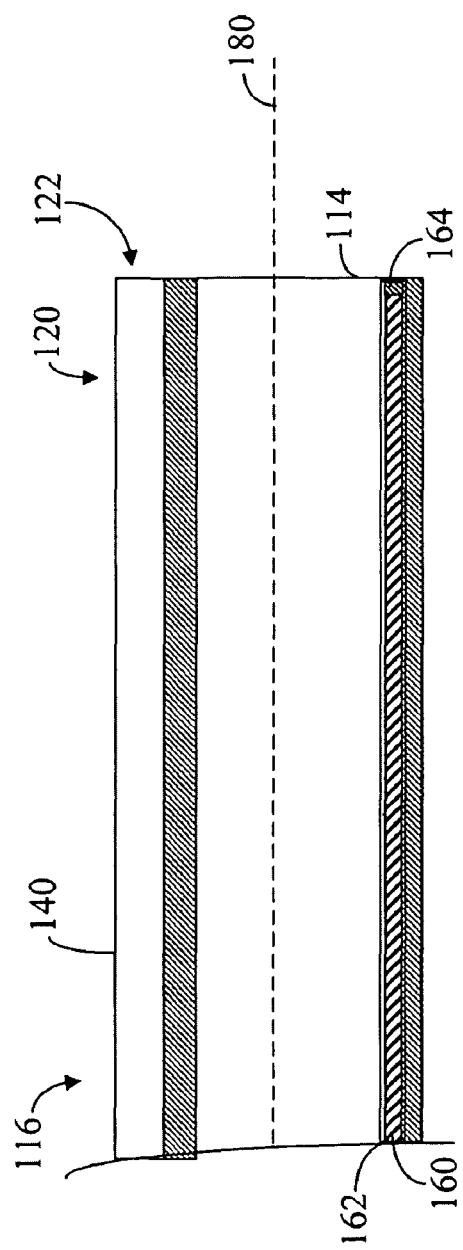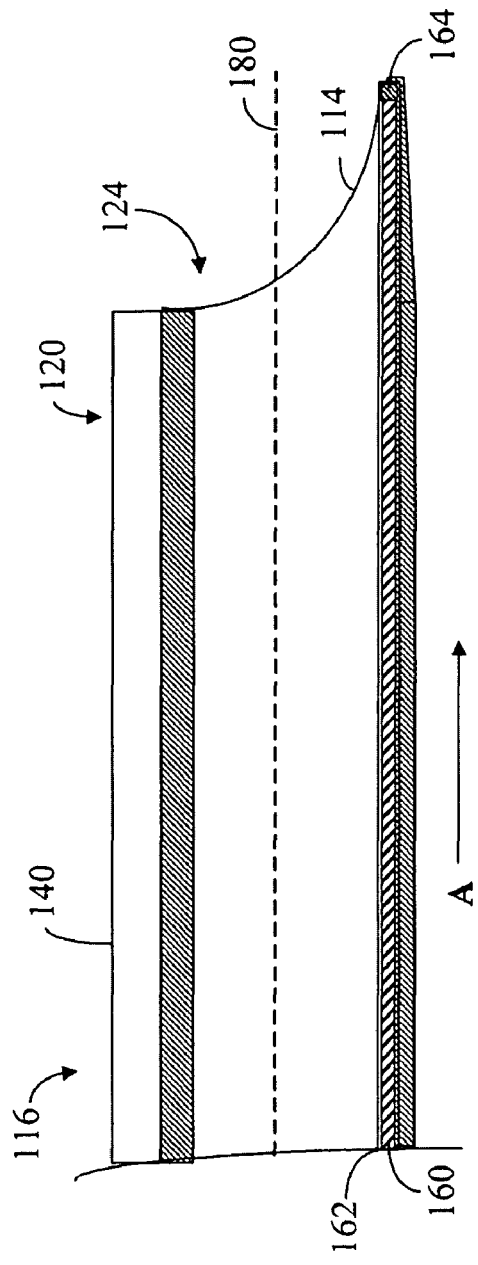

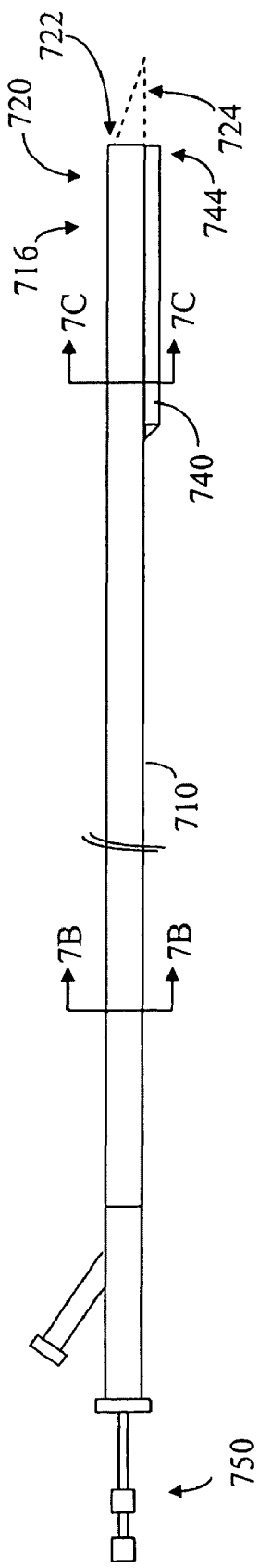
FIG. 7A
FIG. 7B
FIG. 7C

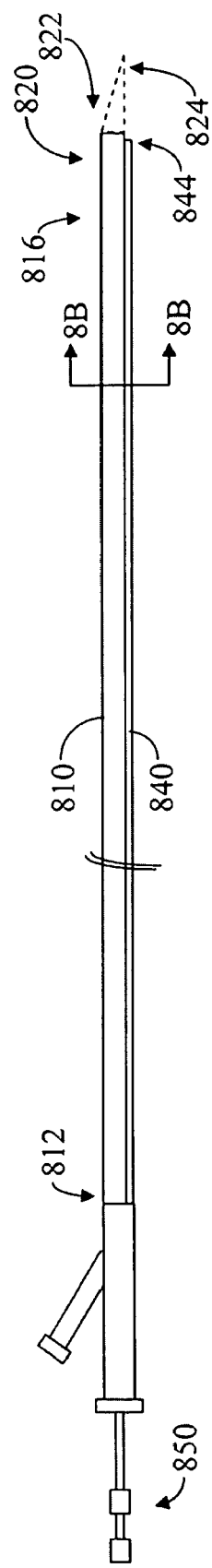
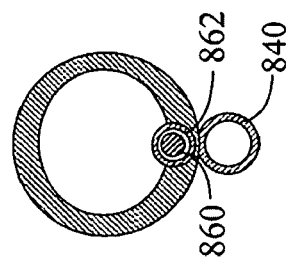
FIG. 8A
800
FIG. 8B

ASPIRATION CATHETER HAVING SELECTIVELY DEFORMABLE TIP

FIELD OF THE INVENTION

The present disclosure relates generally to aspiration catheters and more particularly, to aspiration catheters having a deformable elastic tip.

BACKGROUND OF THE INVENTION

A stenosis, or narrowing of a blood vessel such as an artery may comprise a hard, calcified substance and/or a softer thrombus (clot) material. There have been numerous therapeutic procedures developed for the treatment of stenosis in an artery. One of the better-known procedures is percutaneous transluminal coronary angioplasty (PTCA). According to this procedure, the narrowing in the coronary artery can be reduced by positioning a dilatation balloon across the stenosis and inflating the balloon to re-establish acceptable blood flow through the artery. Additional therapeutic procedures may include stent deployment, atherectomy, and thrombectomy, which are well known and have proven effective in the treatment of such stenotic lesions. Distal occlusion or filtration, with or without aspiration embolectomy, have also been developed to prevent downstream embolization by collecting and removing atheroembolic debris that may be generated during any of the above therapies. Increasingly specialized aspiration catheters have been developed for aspiration of body fluids contaminated with thrombus or embolic debris before, during and/or after an arterial intervention.

One important feature of aspiration catheters is the ability to rapidly and efficiently aspirate large embolic particles without the need to first break them into smaller sub-particles. This advantage is achieved, at least in part, by providing the catheter with an aspiration lumen and aspiration lumen inlet port having as large a cross sectional area as possible, given overall size constraints of the catheter design. However, one drawback to aspiration catheters is that the aspiration lumen opening has a fixed cross sectional area that is unable to increase in size to accommodate larger embolic particles.

Another important feature of aspiration catheters is the tip. Current aspiration catheters have distal tips that have fixed geometry, viz., the tips are either orthogonal or oblique with respect to a longitudinal axis of the catheter. Orthogonal tips are well suited for fully contacting a clot to be aspirated and for aspirating material directly in front of the tip. However, orthogonal tips are not well suited for aspirating material positioned at a side of the aspiration catheter or thrombus adhering to the vessel wall. Oblique tips provide an angled opening suitable for aspirating particles positioned at a side of the aspiration catheter and can improve the removal of thrombus adhering to the vessel wall. However, oblique tips are not well suited for fully contacting a clot directly in front of the tip. Thus, with prior devices having either an orthogonal tip or an oblique tip, a practitioner does not have an aspiration catheter suitable for aspirating particles both in front of aspiration opening and to the side of the opening.

Consequently, a need exists for aspiration catheters that overcome these and other disadvantages.

SUMMARY OF THE INVENTION

One aspect of the invention provides an elongate aspiration catheter for removing emboli or other particles from a blood vessel. The catheter includes an elongate tubular shaft having an aspiration lumen, the aspiration lumen defined by a shaft wall and fluidly connecting a proximal fluid port to an aspiration opening disposed at a distal end of the elongate tubular shaft and an elastically deformable tip disposed at the distal end of the elongate tubular shaft, the elastically deformable tip moveable between an orthogonal configuration and an oblique configuration. The catheter further includes at least one core wire lumen within at least a portion of the shaft wall, the at least one core wire lumen extends longitudinally from the elastically deformable tip to a control handle operably connected to a connector fitting mounted at a proximal end of the elongate tubular member and at least one core wire disposed within the at least one core wire lumen, the at least one core wire extending from the elastically deformable tip to the control handle.

Another aspect of the invention provides a method of treating a vascular condition with an aspiration catheter. The method includes the steps of advancing an aspiration catheter having a deformable elastic tip to a treatment site, advancing at least one core wire operably connected to the deformable elastic tip, deforming the deformable elastic tip to an oblique configuration based on the advancing the at least one core wire and retracting the at least one core wire to move the deformable elastic tip from the oblique configuration to an orthogonal configuration.

BRIEF DESCRIPTION OF THE DRAWINGS

The present invention is illustrated by the accompanying drawings of various embodiments and the detailed description given below. The drawings should not be taken to limit the invention to the specific embodiments but are for explanation and clarity. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings, which are not drawn to scale.

FIG. 1A illustrates a side view of one embodiment of an aspiration catheter made in accordance with the present invention;

FIG. 1B is a cross section of the aspiration catheter shown in FIG. 1A taken along line 1B-1B;

FIG. 1C is a cross section of the aspiration catheter shown in FIG. 1A taken along line 1C-1C;

FIG. 2A illustrates a side view of another embodiment of an aspiration catheter made in accordance with the present invention;

FIG. 2B is a cross section of the aspiration catheter shown in FIG. 2A taken along line 2B-2B;

FIG. 2C is a cross section of the aspiration catheter shown in FIG. 2A taken along line 2C-2C;

FIG. 4A illustrates a side view of another embodiment of an aspiration catheter made in accordance with the present invention;

FIG. 4B is a cross section of the aspiration catheter shown in FIG. 4A taken along line 4B-4B;

FIG. 4C is a cross section of the aspiration catheter shown in FIG. 4A taken along line 4C-4C;

FIGS. 5 and 6 are partial longitudinal cross section views of a distal end of an aspiration catheter made in accordance with the present invention;

FIG. 7A illustrates a side view of another embodiment of an aspiration catheter made in accordance with the present invention;

FIG. 7B is a cross section of the aspiration catheter shown in FIG. 7A taken along line 7B-7B;

FIG. 7C is a cross section of the aspiration catheter shown in FIG. 7A taken along line 7C-7C;

FIG. 8A illustrates a side view of another embodiment of an aspiration catheter made in accordance with the present invention;

FIG. 8B is a cross section of the aspiration catheter shown in FIG. 8A taken along line 8B-8B.

DETAILED DESCRIPTION OF THE INVENTION

Figure 3A:
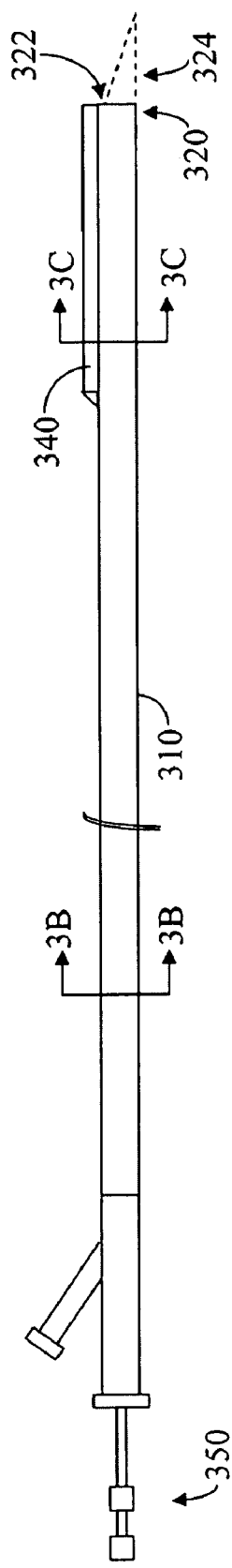
FIG. 3A illustrates a side view of another embodiment of an aspiration catheter made in accordance with the present invention.

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the disclosure or the application and uses of the disclosure. Although the description of the disclosure is in the context of aspiration catheters for treatment of coronary arteries, the disclosure is not so limited, and the disclosure may be useful for other types of catheters and for treatment of other blood vessels. Furthermore, there is no intention to be bound by any expressed or implied theory presented in the preceding technical field, background, brief summary or the following detailed description.

FIGS. 1A to 1C illustrate one embodiment of an aspiration catheter 100, made in accordance with the present invention. FIG. 1A illustrates a side view of aspiration catheter 100. FIG. 1B illustrates a cross section of aspiration catheter 100 taken along line 1B-1B and FIG. 1C illustrates a cross section of aspiration catheter 100 taken along line 1C-1C.

Aspiration catheter 100 is a rapid exchange catheter. Aspiration catheter 100 includes an elongate tubular shaft 110 with a distal end region 116 having an elastically deformable tip 120. Elongate tubular shaft 110 includes an aspiration lumen 118 extending through shaft 110 between open proximal end 112 and open distal port 114. Elongate tubular shaft 110 is attached at proximal end 112 to connector fitting 130. Connector fitting 130 provides a functional access port at proximal end 112 of aspiration catheter 100. Connector fitting 130 is attached to catheter shaft 110 and has a central passageway in communication with open proximal end 112 and aspiration lumen 118 to allow passage of various fluids. Connector fitting 130 further includes an adaptor 132 in fluid communication with aspiration lumen 118 and adapted for connection to a vacuum source (not shown) to aspirate blood and particulates through aspiration lumen 118. In the field of aspiration catheters, the terms suction, vacuum, partial vacuum, reduced pressure, and negative pressure are all used interchangeably.

Aspiration catheter 100 includes a guidewire tube 140 having a guidewire lumen 142 extending therethrough between open ends 144, 146. Guidewire tube 140 is substantially shorter than the full length of catheter 100. Guidewire tube 140 extends proximally from open distal end 144 disposed at or adjacent the distal end 116 of elongate tubular shaft 110 to open proximal end 146 of guidewire lumen 142. As shown in FIG. 1C, guidewire tube 140 and elongate tubular shaft 110 are arranged in a parallel or side-by-side configuration. Guidewire tube 140 may be attached to elongate tubular shaft 110 by any suitable securement means such as, for example, an adhesive, a solvent bond or an over sleeve surrounding guidewire tube 140 and elongate tubular shaft 110.

Elongate tubular shaft 110 may be comprised of a single material or may be a multi-layer composite. As shown in FIG. 1B, in one embodiment, elongate tubular shaft 110 comprises an outer polymeric layer 111, an inner polymeric layer 113 and a reinforcement layer 115 disposed between outer polymeric layer 111 and inner polymeric layer 113. Inner polymeric layer 113 defines aspiration lumen 118.

Elongate tubular shaft 110 may be composed of any suitable biocompatible material or combination of materials. Outer polymeric layer 111 and inner polymeric layer 113 may be composed of the same or different biocompatible materials such as, for example, polyamide, polyethylene block amide copolymer (PEBA), fluoropolymers (e.g. PTFE, FEP), polyolefins (e.g. polypropylene, high-density polyethylene), or high density polyamides.

Reinforcement layer 115 is positioned between and is substantially coaxial with outer polymeric layer 111 and inner polymeric layer 113. Reinforcement layer 115 resists collapse of lumen 118 during aspiration, and enhances the torsional strength and inhibits kinking of shaft 110 during advancement of catheter 100 within the patient's vasculature. As shown in FIGS. 1B and 1C, in some embodiments of the present invention shaft 110 includes reinforcement layer 115 within a proximal portion 117 of shaft 110 and does not include reinforcement layer 115 in a distal region 116 of shaft 110. Reinforcement layer 115 is omitted in distal portion to increase flexibility of the distal portion of shaft 110. In various embodiments, reinforcement layer 115 may be formed by braiding multiple filaments or winding at least one filament over inner polymeric layer 113 or by applying a metal mesh over inner polymeric layer 113. Braided or wound filaments may comprise high-modulus thermoplastic or thermo-set plastic materials, such as, for example, liquid crystal polymer (LCP), polyester, or aramid polymer. Alternatively, braided or wound filaments may comprise metal wires of stainless steel, superelastic alloys such as nitinol (TiNi), refractory metals such as tantalum, or a work-hardenable super alloy comprising nickel, cobalt, chromium and molybdenum. The reinforcing filaments may have cross sections that are round or rectangular.

Outer polymeric layer 111 provides support to catheter shaft 110 and coverage of reinforcement layer 115. Outer polymeric layer 111 is coaxial with inner polymeric layer 113 and reinforcement layer 115, and may be a single or unitary tube that continuously extends from proximal end 112 to distal end 116 of shaft 110. Outer polymeric layer 115 may be thermoplastically extruded over, and forced into any interstices in, reinforcement layer 115 to promote adhesion between the outer and inner polymeric layers and to encapsulate reinforcement layer 115.

Aspiration catheter 100 includes an elastically deformable tip 120 disposed at the distal end region 116 of shaft 110. Elastically deformable tip 120 is composed of a soft elastic material, such as, for example, silicone elastomer, viscous forms of natural and synthetic rubbers such as polybutylene, polyisobutylene, polybutadiene, polyethylene, styrenebutadiene copolymers, polyisoprene, polyurethane, ethylene/propylene copolymers, polyalkylacrylate polymers, copolyesters, ethylene/acrylic copolymers, butadiene/acrylonitrile copolymers, and ethylene vinylacetate (EVA) polymers. As shown in FIGS. 5 and 6 and described in more detail below, at least a portion of the elastically deformable tip 120 extends from an orthogonal configuration 122 to an oblique configuration 124 (shown as dotted line in FIG. 1A) when force is applied via at least one core wire 160 embedded within the distal end 116 of shaft 110. The extent to which the elastically deformable tip 120 extends into the oblique configuration 124 may vary depending on a particular application and the soft elastic material used to form the elastically deformable tip 120. In exemplary embodiments, the elastically deformable tip 120 extends to a length that is about two to ten times the diameter of the aspiration lumen opening. In one embodiment, the elastically deformable tip extends to a length that is about four times the diameter of the aspiration lumen opening. In one embodiment, the aspiration lumen diameter is 0.044 inches and the deformable elastic tip extends from the orthogonal configuration to an oblique configuration having a length of 0.167 inches.

Changing the orthogonal configuration of the elastically deformable tip 120 to an oblique configuration increases the area or size of the aspiration port 114. In use, a practitioner may encounter a particulate or thrombus of a size that is too large to fit through an orthogonal aspiration port 114. To try to accommodate this large material, the practitioner may deform the elastically deformable tip to an oblique configuration thereby altering aspiration port 114 from a generally circular shape to a generally elliptical shape having an elongate major axis and a larger open area.

Referring to FIGS. 1A, 1B, 1C, 5 and 6, core wire 160 is disposed within core wire lumen 162. Core wire lumen 162 is parallel to aspiration lumen 118. Core wire lumen 162 extends from control handle 150 to distal end region 116 of shaft 110. Core wire 160 is composed of a metallic material, a rigid polymeric material or combinations thereof. Discussed in more detail below, FIGS. 2A to 4C illustrate several embodiments of aspiration catheters having various arrangements of core wires and core wire lumens made in accordance with the present invention. In one embodiment, core wire 160 includes a stop 164 disposed at a distal end of core wire 160. Stop 164 is configured to prevent core wire 160 from piercing the distal end of the shaft wall. In one embodiment, stop 164 comprises a polymer cap covering the distal end of core wire 160. In another embodiment, stop 164 comprises a block or ring of relatively hard material within the inner and/or outer polymeric layer having a surface that abuts the distal end of core wire 160. In one embodiment, stop 164 comprises a radiopaque marker composed of radiopaque material that may aid in the visualization of the distal end of aspiration catheter 100. In another embodiment, a distal end of core wire 160 and/or a stop 164 is embedded in the material composing elastically deformable tip 120. Such embedment securely anchors the core wire distal end in tip 120 to permit the core wire to transform the tip by either pushing distally or pulling proximally on the material of tip 120.

With further reference to FIGS. 5 and 6, FIG. 5 illustrates elastically deformable tip 120 in orthogonal configuration 122 wherein aspiration port 114 is orthogonal to longitudinal axis 180. FIG. 6 illustrates elastically deformable tip 120 in oblique configuration 124. As shown in FIG. 6, when axial force (designated by arrow A) is applied in the distal direction to core wire 160, core wire 160 advances longitudinally within lumen 162, causing a portion of elastically deformable tip 120 to extend into oblique configuration 124. In this embodiment, the portion of elastically deformable tip 120 that extends into oblique configuration 124, i.e., the leading edge of tip 120 is positioned opposite of guidewire tube 140. As discussed below, in some embodiments, the portion of elastically deformable tip 120 that extends varies depending on the core wire or core wires that are advanced longitudinally.

Referring to FIG. 1A, FIG. 1A schematically illustrates control handle 150. Control handle 150 is operably disposed at a proximal end of connector fitting 130. Control handle 150 is operably connected to core wire 160. Actuation of control handle 150 advances and retracts core wire 160 within lumen 162. In one embodiment, control handle 150 includes push/pull knob 154 and locking knob 152. Push/pull knob 154 is operably connected to a proximal end of core wire 160. Push/pull knob 154 advances and retracts core wire 160. Locking knob 152 is operably connected to a proximal end of core wire lumen 162 and may be used to lock core wire 160 into a desired position such that elastically deformable tip 120 may be locked in the orthogonal configuration 122 or oblique configuration 124. In one embodiment, core wire 160 is locked in position by rotation of locking knob 152 in either a clockwise or counter-clockwise direction. Core wire 160 is unlocked by rotating locking knob 152 in the opposite direction. In one embodiment, elastically deformable tip 120 may be placed and locked in a variety of angles between the fully retracted orthogonal configuration 122 to the fully expanded oblique configuration 124. The degree to which the elastically deformable tip 120 is extended may be chosen by the practitioner to suit the particular need as determined by the location and type of liquid or particulate matter to be aspirated. Those with skill in the art will appreciate that the control handle may take other forms suitable for advancing and retracting one or more core wires. In another embodiment, a control handle may comprise a roller or thumb wheel type controller operably connected to core wire 160. In another embodiment, control handle 150 may comprise a joystick-type controller.

FIGS. 2A to 2C illustrate another embodiment of an aspiration catheter 200 made in accordance with the present invention. Many aspects of aspiration catheter 200 are the same as or similar to aspiration catheter 100 and will not be discussed further. In this embodiment and those described below, reinforcement layer has been omitted from the drawing (FIG. 2B) for clarity. Aspiration catheter 200 differs from aspiration catheter 100 in the number and placement of core wires and core wire lumens. As best shown in FIGS. 2B and 2C, aspiration catheter 200 includes first core wire 260*a* disposed in core wire lumen 262*a* and second core wire 260*b* disposed in core wire lumen 262*b*. Core wire lumens 262*a*, 262*b* are disposed within shaft 210 at positions opposite guide wire tube 240. Using a clock analogy, core wire lumens 262*a*, 262*b* are disposed around the circumference of shaft 210 at approximately 7 o'clock and 5 o'clock, respectively. Proximal ends of core wires 260*a*, 260*b* are operably connected to control handle 250. In one embodiment, core wires 260*a*, 260*b* are independently controllable. In this embodiment, a practitioner may advance and retract core wire 260*a*, core wire 260*b* or both core wires to move elastically deformable tip 220 between orthogonal configuration 222 and oblique configuration 224. In one method of using catheter 200, one of core wires 260*a*, 260*b* is held in place or retracted slightly while the other core wire 260*a* or 260*b* is advanced. In this embodiment, the simultaneous retraction of one core wire and the advancement of another core wire prevents or reduces deflection of tip 220 away from the catheter's longitudinal axis, as may result from the advancement of a single core wire.

Figure 3C:
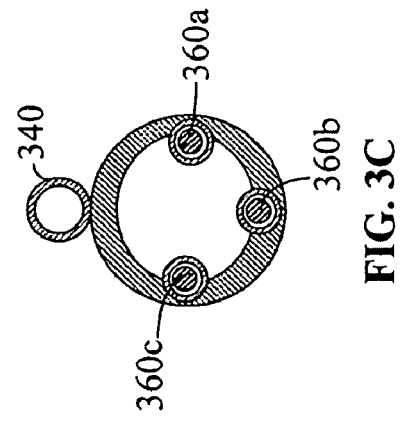
FIG. 3C is a cross section of the aspiration catheter shown in FIG. 3A taken along line 3C-3C.
Figure 3B:
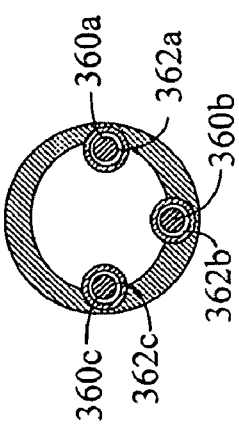
FIG. 3B is a cross section of the aspiration catheter shown in FIG. 3A taken along line 3B-3B.

FIGS. 3A to 3C illustrate another embodiment of an aspiration catheter 300 made in accordance with the present invention. Many aspects of aspiration catheter 300 are the same as or similar to aspiration catheters 100, 200 and will not be discussed further. Aspiration catheter 300 differs from aspiration catheters 100, 200 in the number and placement of core wires and core wire lumens. As best shown in FIGS. 3B and 3C, aspiration catheter 300 includes first core wire 360a disposed in core wire lumen 362a, second core wire 360b disposed in core wire lumen 362b and third core wire 360c disposed in core wire lumen 362c. Core wire lumens 362a, 362b, 362c are disposed within shaft 310 at positions spaced from guide wire tube 340. Again using the clock analogy, core wire lumens 362a, 362b, 362c are disposed around the circumference of shaft 310 at approximately 3 o'clock, 6 o'clock and 9 o'clock, respectively. Proximal ends of core wires 360a, 360b, 360c are operably connected to control handle 350. In one embodiment, core wires 360a, 360b, 360c are independently controllable. In this embodiment, a practitioner may advance and retract core wire 360a, 360b, or 360c singly, in pairs or all core wires 360a, 360b, 360c to move elastically deformable tip 320 between orthogonal configuration 322 and oblique configuration 324. In one embodiment, core wires 360a, 360c are held in place or retracted slightly while core wire 360b is advanced. In this embodiment, the simultaneous holding or retraction of core wires 360a, 360c and the advancement of core wire 360b prevents or reduces deflection of tip 320 away from the catheter's longitudinal axis, as may result from the advancement of a single core wire.

In the illustrated embodiment of catheter 300, elastically deformable tip 320 is formed, in its relaxed state, to have orthogonal configuration 322, which can be reversibly transformed into oblique configuration 324 by, for example, pushing one or more core wires in a distal direction. In an alternative embodiment, elastically deformable tip 320 is formed, in its relaxed state, to have oblique configuration 324, which can be reversibly transformed into orthogonal configuration 322 by, for example pulling one or more core wires in a proximal direction. One of skill in the art will recognize that any arrangement of core wires may be advanced, held or retracted based on a particular need of the practitioner. In use, a practitioner may extend elastically deformable tip 320 as well as deflect the tip by advancing at least one of core wires 360a, 360b, 360c and not simultaneously holding or retracting a remaining core wire, if any.

FIGS. 4A to 4C illustrate another embodiment of an aspiration catheter 400 made in accordance with the present invention. Many aspects of aspiration catheter 400 are the same as or similar to aspiration catheters 100, 200, 300 and will not be discussed further. Aspiration catheter 400 differs from aspiration catheters 100, 200, 300 in the number and placement of core wires and core wire lumens. As best shown in FIGS. 4B and 4C, aspiration catheter 400 includes a plurality of core wires 460 and core wire lumens 462 substantially evenly distributed about the circumference of shaft 410. Proximal ends of core wires 460 are operably connected to control handle 450.

In another embodiment, core wires 460 are independently controllable. In this embodiment, a practitioner may advance and retract core wires 460 singly, in pairs, or multiples to move elastically deformable tip 420 between orthogonal configuration 422 and a variety of oblique configurations such as oblique configurations 424a to 424d. As described above, a practitioner may simultaneously hold or retract one or more core wires while advancing one or more other core wires 460 in order to move a selected portion of the elastically deformable tip 420 from an orthogonal configuration to the desired oblique configuration 424a to 424d. In this embodiment, the simultaneous holding or retraction of a first portion of core wires 460 and the advancement of a second portion of core wires 460 prevents or reduces deflection of tip 420 away from the catheter's longitudinal axis, as may result from the advancement of a single core wire. One of skill in the art will recognize that any arrangement of core wires may be advanced, held or retracted based on a particular need of the practitioner. In use, a practitioner may extend elastically deformable tip 420 as well as deflect the tip by advancing at least one of core wires 460 and not simultaneously holding or retracting a remaining core wire.

In one embodiment, control handle 450 comprises a selective controller for selectively engaging a portion of the plurality of core wires. In this embodiment, the selective controller includes an engagement device that is oriented to engage a selected portion of core wires 460. In one embodiment, the engagement device comprises a half-moon shaped push/pull rod that may be rotated by a clinician to select a desired plurality of core wires.

FIGS. 7A to 7C illustrate another embodiment of an aspiration catheter 700 made in accordance with the present invention. Many aspects of aspiration catheter 700 are the same as or similar to aspiration catheters 100, 200, 300, 400 and will not be discussed further. Aspiration catheter 700 is a rapid exchange catheter similar to the rapid exchange catheters described above. However, aspiration catheter 700 differs from aspiration catheters 100, 200, 300, 400 in the placement of guidewire tube 740 and in relation to the deformable portion of elastically deformable tip 720 and the location of the core wire 760 and core wire lumen 762. In this embodiment, the deformable portion of elastically deformable tip 720 is located on the same side of shaft 710 to which the guidewire tube 740 is secured. In this embodiment, guidewire tube 740 is attached to the distal end 716 of shaft 710 in a manner that does not interfere with the extension and retraction of elastically deformable tip 720. In one embodiment, the distal end 744 of guidewire tube 740 is slightly proximal to the distal end 716 of shaft 710. Similar to aspiration catheters 100, 200, 300, 400, proximal end of core wire 760 is operably connected to control handle 750. As before, advancement and retraction of core wire 760 moves elastically deformable tip 720 between an orthogonal configuration 722 and an oblique configuration 724.

FIGS. 8A and 8B illustrate another embodiment of an aspiration catheter 800 made in accordance with the present invention. Many aspects of aspiration catheter 800 are the same as or similar to aspiration catheters 100, 200, 300, 400, 700 and will not be discussed further. Aspiration catheter 800 is an over-the-wire catheter. Aspiration catheter 800 differs from aspiration catheters 100, 200, 300, 400, 700 in the configuration and placement of guidewire tube 840. In this embodiment, guidewire tube 840 extends from proximal end 812 of shaft 810 to distal end region 816. In this embodiment, the deformable portion of elastically deformable tip 820 is located on the same side of shaft 810 to which the guidewire tube 840 is secured. In this embodiment, the leading edge of the deformable elastic tip is on the same side as the surface to which the guidewire tube is attached. In this embodiment, guidewire tube 840 is attached to the distal end region 816 of shaft 810 in a manner that does not interfere with the extension and retraction of elastically deformable tip 820. In one embodiment, the distal end 844 of guidewire tube 840 is slightly proximal to the distal end 816 of shaft 810. Similar to aspiration catheters 100, 200, 300, 400, 700, proximal end of core wire 860 is operably connected to control handle 850. As before, advancement and retraction of core wire 860 moves elastically deformable tip 820 between an orthogonal configuration 822 and an oblique configuration 824. Those with skill in the art will recognize that the arrangements of core wires 860 and core wire lumens 862 is not limited to that illustrated in FIGS. 8A and 8B. The arrangement of core wires and core wire lumens illustrated in FIGS. 1A to 7C may be adapted for use in over-the-wire aspiration catheter 800.

Figure 9:
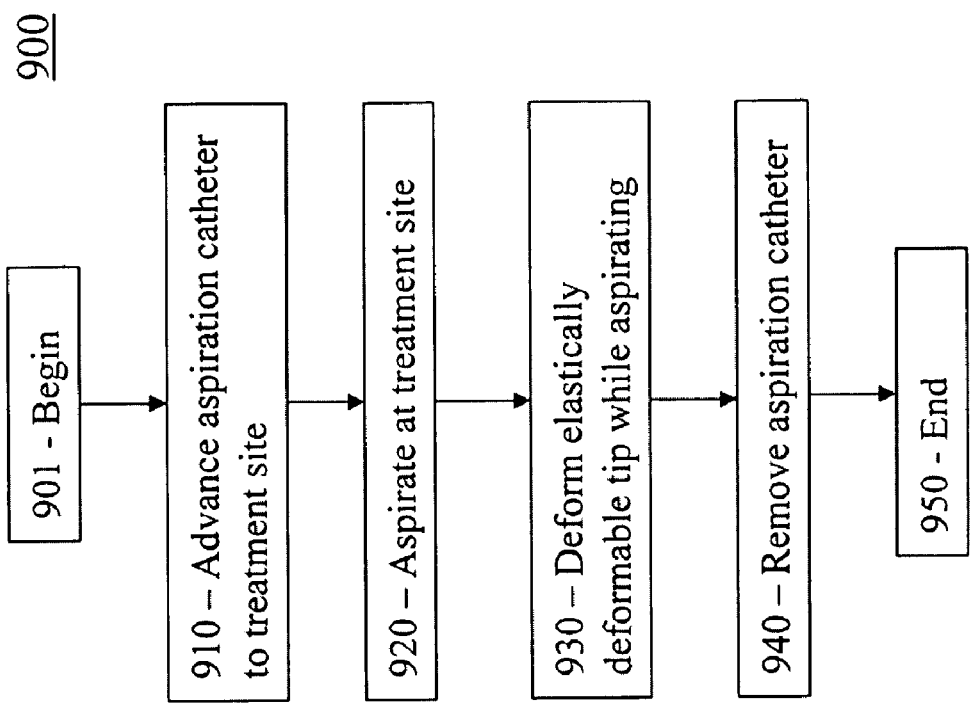
FIG. 9 is a flow chart of one embodiment of a method of using an aspiration catheter in accordance with the present invention.

FIG. 9 is a flow chart of one method 900 of treating a vascular condition using any of the aspiration catheters 100, 200, 300, 400, 700, 800 having an elastically deformable tip, as described above and illustrated in FIGS. 1A to 8B. Method 900 begins at 901. An aspiration catheter is advanced over a guidewire through the vasculature to a treatment site such as a coronary artery (Block 910). Aspiration of liquid or particulate matter (thrombus) may begin by application of a vacuum via a vacuum source operably connected to connector fitting 130 (Block 920). As needed to appose the tip with thrombus or other material to be aspirated, the practitioner may transform the configuration of the elastically deformable tip by advancing and retracting a core wire 160 operably connected at a distal end to the elastically deformable tip 120 and connected at a proximal end to a control handle 150 (Block 930). Alternatively, the aspiration step may be delayed until after the tip has been transformed and positioned as desired. In one embodiment, at least one core wire is retracted or held stationary while at least one other core wire is longitudinally advanced to extend the elastically deformable tip. In another embodiment, a first portion of core wires is held stationary or retracted while a second portion of core wires is longitudinally advanced to extend the elastically deformable tip. In another embodiment, the elastically deformable tip is extended and deflected by longitudinally advancing a core wire. The aspiration catheter is removed upon completion of the treatment procedure (Block 940). Method 900 ends at 950.

While the invention has been described with reference to particular embodiments, it will be understood by one skilled in the art that variations and modifications may be made in form and detail without departing from the spirit and scope of the invention.

What is claimed is:

1. An elongate aspiration catheter for removing emboli or other particles from a blood vessel, the catheter comprising:
   an elongate tubular shaft having an aspiration lumen defined by a shaft wall and fluidly connecting a proximal fluid port to an aspiration port disposed at a distal end of the elongate tubular shaft;
   an elastically deformable tip disposed at the distal end of the elongate tubular shaft, the tip defining the aspiration port and being deformable to enable manipulation of the aspiration port between orthogonal and oblique configurations;
   at least one core wire lumen within at least a portion of the shaft wall, the at least one core wire lumen extending longitudinally from the elastically deformable tip to a control handle operably connected to a connector fitting mounted at a proximal end of the elongate tubular member; and
   at least one core wire slidably disposed within the at least one core wire lumen and operatively connected, at its distal end, to the tip and extending from the elastically deformable tip to the control handle;
   wherein the elastically deformable tip is reversibly transformable between varying configurations in which the aspiration port is selectively shaped in orthogonal or oblique shapes in response to longitudinally directed force applied to the tip by the at least one core wire.

2. The aspiration catheter of claim 1 further comprising a guidewire tube extending alongside and secured to at least a distal region of the elongate tubular shaft.

3. The aspiration catheter of claim 1 wherein at least a portion of the elongate tubular shaft comprises an outer polymeric layer, and inner polymeric layer and a reinforcement layer disposed between the outer polymeric layer and the inner polymeric layer.

4. The aspiration catheter of claim 1 wherein the deformable tip is elastically extendable by a length equal to about 2 to about 10 times the diameter of the aspiration lumen.

5. The aspiration catheter of claim 4 wherein the aspiration lumen diameter is about 0.04 inches.

6. The aspiration catheter of claim 1 wherein the elastically deformable tip comprises a soft polymeric material.

7. The aspiration catheter of claim 6 wherein the soft polymeric material is chosen from a group consisting of silicone elastomer, viscous forms of natural and synthetic rubbers, polybutylene, polyisobutylene, polybutadiene, polyethylene, styrenebutadiene copolymers, polyisoprene, polyurethane, ethylene/propylene copolymers, polyalkylacrylate polymers, copolyesters, ethylene/acrylic copolymers, butadiene/acrylonitrile copolymers, and ethylene vinylacetate (EVA) polymers.

8. The aspiration catheter of claim 1 further comprising the tip having a stop disposed to engage the distal end of the at least one core wire.

9. The aspiration catheter of claim 1 wherein at least one core wire comprises a first core wire disposed within a first core wire lumen and a second core wire disposed within a second core wire lumen.

10. The aspiration catheter of claim 1 wherein the at least one core wire comprises a first core wire disposed within a first core wire lumen, a second core wire disposed within a second core wire lumen and a third core wire disposed within a third core wire lumen.

11. The aspiration catheter of claim 1 wherein the control handle comprises a selective controller adapted to control the longitudinal position of its associated core wire.

12. The aspiration catheter of claim 1 wherein the at least one core wire comprises a plurality of core wires disposed circumferentially about the aspiration lumen.

13. The aspiration catheter of claim 12 wherein the control handle comprises a selective controller for selectively controlling the longitudinal position of the plurality of core wires.

14. The aspiration catheter of claim 2 wherein the guidewire tube is secured to the elongated tubular shaft by a securement means selected from an adhesive, a solvent bond, and an over sleeve surrounding the guidewire tube and the elongate tubular member.

15. The aspiration catheter of claim 14 wherein the guidewire tube comprises a rapid exchange guidewire tube secured to a surface of a distal region of the elongated tubular shaft positioned opposite a leading edge of the elastically deformable tip.

16. The aspiration catheter of claim 14 wherein the guidewire tube comprises a rapid exchange guidewire tube secured to a surface of a distal portion of the elongated tubular shaft positioned adjacent a leading edge of the elastically deformable tip.

17. The aspiration catheter of claim 3 wherein the reinforcement layer comprises a tubular braid.

* * * * *